US00RE34875E

United States Patent [19]

Birmingham et al.

[11] E Patent Number: Re. 34,875

[45] Reissued Date of Patent: Mar. 14, 1995

[54] METHOD OF SELECTING RECOMBINANT DNA-CONTAINING STREPTOMYCES

[75] Inventors: Virginia A. Birmingham, Carmel, Tex.; Eugene T. Seno, Indianapolis, Ind.

[73] Assignee: Eli Lilly and Company, Indianapolis, Ind.

[21] Appl. No.: 985,512

[22] Filed: Dec. 2, 1992

Related U.S. Patent Documents

Reissue of:

[64] Patent No.: 4,680,265
Issued: Jul. 14, 1987
Appl. No.: 653,975
Filed: Sep. 25, 1984

U.S. Applications:

[63] Continuation of Ser. No. 762,048, Sep. 18, 1991, abandoned, which is a continuation of Ser. No. 641,624, Jan. 16, 1991, abandoned, which is a continuation of Ser. No. 376,344, Jul. 6, 1989, abandoned.

[51] Int. Cl.[6] ..... C12N 15/00; C12N 15/11

[52] U.S. Cl. ..... 435/172.3; 435/252.3; 435/252.35; 435/320.1; 536/23.1; 536/23.2; 536/23.7

[58] Field of Search ..... 435/69.1, 71.3, 91, 435/172.1, 172.3, 252.3–252.35, 320.1, 886, 889; 536/23.7, 23.2, 23.1; 935/6, 14, 29, 72, 75

[56] References Cited

U.S. PATENT DOCUMENTS 4,416,994 11/1983 Nakatsukasa et al. ..... 435/252.33
4,468,462 8/1984 Malin et al. ..... 435/252.3

FOREIGN PATENT DOCUMENTS 0176319 4/1986 European Pat. Off. ..... 435/172.3
0251510 1/1988 European Pat. Off. ..... 435/172.3
0254576 1/1988 European Pat. Off. ..... 435/172.3

OTHER PUBLICATIONS

Benveniste and Davies, 1973, *Proceedings of the National Academy of Sciences, USA* 70(8):2276.
Thompson et al., 1980, *Nature* 286:525.
Thompson et al., 1982, *Gene* 20:51.
Katz et al., *J. Gen. Microbiology,* 129:2703 (1983).

*Primary Examiner*—James Martinell
*Attorney, Agent, or Firm*—Richard B. Murphy; Gerald V. Dahling

[57] ABSTRACT

A novel method of selecting Streptomyces recombinant DNA-containing host cells and vectors useful in the method are described. The vectors confer tylosin resistance to sensitive Streptomyces host cells and thus provide a convenient method of selecting Streptomyces transformants. The novel tylosin resistance-conferring gene described can be isolated on an ~2.6 kb KpnI restriction fragment from plasmid pSVB2. Plasmid pSVB2 can be isolated from Streptomyces lividans TK23/pSVB2 (NRRL 15880).

56 Claims, 10 Drawing Sheets

Restriction Site and Function Map of Plasmid pSVB2 (10.63 kb)

Restriction Site and Function Map of Plasmid pIJ702 (5.65 kb)

Restriction Site and Function Map of Plasmid pSVB12 (8.25 kb)

Restriction Site and Function Map of Plasmid pSVB23 (8.25 kb)

Restriction Site and Function Map of Plasmid pSVB16 (9.49 kb)

Restriction Site and Function Map of Plasmid pSVB18 (9.49 kb)

Restriction Site and Function Map of Plasmid pSVB20 (8.46 kb)

Restriction Site and Function Map of Plasmid pSVB22 (8.46 kb)

Restriction Site and Function Map of Phage pSVB3310 (41.47 kb)

Restriction Site and Function Map of Phage pSVB3311 (41.47 kb)

METHOD OF SELECTING RECOMBINANT DNA-CONTAINING STREPTOMYCES

Matter enclosed in heavy brackets [ ] appears in the original patent but forms no part of this reissue specification; matter printed in italics indicates the additions made by reissue.

*This application is a continuation of application Ser. No. 07/762,048, filed on Sep. 18, 1991, now abandoned, which is a continuation of application Ser. No. 07/641,624, filed on Jan. 16, 1991, now abandoned, which is a continuation of Ser. No. 07/376,344, filed on Jul. 6, 1989, now abandoned, which is a reissue of U.S. Pat. No. 4,680,265.*

SUMMARY OF THE INVENTION

The present invention is a method for selecting a recombinant DNA-containing Streptomyces host cell. The invention further comprises recombinant DNA cloning vectors and transformants useful in executing the method.

The present method provides tylosin resistance-conferring cloning vectors for use in Streptomyces. The development and exploitation of recombinant DNA technology in Streptomyces is dependent upon the availability of selectable genetic markers on suitable cloning vectors. This development has been somewhat retarded by the low number of selectable markers presently available for use in Streptomyces. The present invention is useful and especially important in that it expands the number of selectable markers suitable for such use.

The vectors of the present method are particularly useful because they are small, versatile and can be transformed and selected in any Streptomyces cell that is sensitive to tylosin. Streptomyces provides over half of the clinically important antibiotics and thus is a commercially significant group. The present invention provides new and useful cloning systems and vectors for this industrially important group and allows for the cloning of genes both for increasing the yields of known antibiotics, as well as for the production of new antibiotics and antibiotic derivatives.

The present invention further provides a method of selecting Streptomyces transformants from a background of untransformed cells. The method allows one to add non-selectable DNA to the present vectors, transform Streptomyces with the modified vectors and select tylosin-resistant transformants containing this otherwise non-selectable DNA. Since transformation is a very low frequency event, such a functional test is a practical necessity for determining which cell(s), of among the millions of cells, has acquired the transforming DNA.

For purposes of the present invention, as disclosed and claimed herein, the following terms are defined below.

Recombinant DNA Cloning Vector—any autonomously replicating or integrating agent, including, but not limited to, plasmids, comprising a DNA molecule to which one or more additional DNA segments can be or have been added.

Transformation—the introduction of DNA into a recipient host cell that changes the genotype and results in a change in the recipient cell.

Transfectant—a recipient host cell that has undergone transformation by phage DNA.

Transformant—a recipient host cell that has undergone transformation.

Sensitive Host Cell—a host cell that cannot grow in the presence of a given antibiotic without a DNA segment that provides resistance thereto.

Restriction Fragment—any linear DNA molecule generated by the action of one or more restriction enzymes.

Phasmid—a recombinant DNA vector that may act as a phage or as a plasmid.

$Ap^R$—the ampicillin-resistant phenotype
$tsr^R$—the thiostrepton-resistant phenotype
$tyl^R$—the tylosin-resistant phenotype
$Tc^R$—the tetracycline-resistant phenotype
mel—the tyrosinase gene

DETAILED DESCRIPTION OF THE INVENTION

The present invention is a method for selecting a recombinant DNA-containing Streptomyces host cell, said method comprising:

(1) transforming a tylosin-sensitive, restrictionless Streptomyces host cell with a recombinant DNA cloning vector capable of autonomous replication or integration in said Streptomyces host cell, said vector comprising a DNA sequence that confers resistance to tylosin, and (2) culturing said transformed cell under conditions suitable for selection for tylosin resistance, subject to the limitation that said host cell is susceptible to transformation, cell division and culture. The present invention further comprises the vectors and transformants used to practice the aforementioned method.

The present method for selecting Streptomyces transformants by the tylosin-resistant phenotype is best exemplified by transforming Streptomyces lividans TK23 with plasmid pSVB2 and selecting the resulting transformants on tylosin-containing media. Plasmid pSVB2 comprises a novel tylosin resistance-conferring gene that was isolated from Streptomyces fradiae and cloned into plasmid pIJ702. Plasmid pSVB2 can be obtained from Streptomyces lividans TK23/pSVB2, a strain deposited and made part of the permanent stock culture collection of the Northern Regional Research Laboratory, Agricultural Research Service, 1815 North University Street, U.S. Department of Agriculture, Peoria, IL 61604, under the accession number NRRL 15880. A restriction site and function map of plasmid pSVB2 is presented in FIG. 1 of the accompanying drawings.

As shown in FIG. 1, the ~2.6 kb KpnI restriction fragment of plasmid pSVB2 contains the entire tylosin resistance-conferring gene of the present invention. Knowing the location of the tylosin resistance-conferring gene allows for construction of other cloning vectors also useful in the present method. Thus, plasmids pSVB12 and pSVB23 were constructed by inserting the ~2.6 kb tylosin resistance-conferring KpnI restriction fragment into the KpnI site of plasmid pIJ702. The two resultant plasmids, pSVB12 and pSVB23, differ only with respect to the orientation of the inserted fragment. The plasmid pIJ702 starting material can be obtained from Streptomyces lividans/pIJ702, a strain deposited and made part of the permanent stock culture collection of the American Type Culture Collection, 12301 Parklawn Drive, Rockville, MD 20852, under the accession number ATCC 39155. Restriction site and function maps of plasmids pIJ702, pSVB12 and pSVB23 are respectively presented in FIGS. 2, 3 and 4 of the accompanying drawings.

Plasmids pSVB16 and pSVB18 were constructed by inserting the ~3.8 kb PstI restriction fragment of plasmid pSVB2 into the PstI site of plasmid pIJ702. Again, two plasmids resulted because of the two possible orientations of the inserted fragment. Plasmids pSVB16 and pSVB18 are useful in the present method, because the inserted fragment contains the ~2.6 kb KpnI tylosin resistance-conferring restriction fragment of plasmid pSVB2. Restriction site and function maps of plasmids pSVB16 and pSVB18 are respectively presented in FIGS. 5 and 6 of the accompanying drawings.

Additional illustrative plasmids were constructed by inserting the ~2.9 kb BamHI-BglII restriction fragment of plasmid pSVB2 into the BglII site of plasmid pIJ702, thus inactivating the tyrosinase gene present in plasmid pIJ702. Although the resultant plasmids, designated as pSVB20 and pSVB22, differ with respect to the orientation of the inserted fragment, both confer tylosin resistance to tylosin-sensitive Streptomyces host cells. Restriction site and function maps of plasmids pSVB20 and pSVB22 are respectively presented in FIGS. 7 and 8 of the accompanying drawings.

Restriction fragments used to construct vectors illustrative of the present invention can be conventionally modified to facilitate ligation. For example, molecular linkers can be provided to a particular tylosin resistance gene-containing restriction fragment or to DNA comprising replication or integration functions. Thus, specific sites for subsequent ligation can be constructed conveniently. In addition, the various tylosin resistance gene-containing restriction fragments, origin of replication or integration sequences can be modified by adding, eliminating or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that the ~2.6 kb KpnI tylosin resistance gene-containing restriction fragment is not limited to a particular position on a cloning vector, as long as the critical vector-controlled functions are not disrupted. Those skilled in the art understand or can readily determine which sites on a vector are advantageous for the ligation or insertion of a particular tylosin resistance gene-containing restriction fragment.

Although the above-described vectors comprise the Streptomyces replicon derived from plasmid pIJ702, a variety of known Streptomyces replicons can be used to construct similar vectors. Table 1 is an illustrative, but not comprehensive, listing of Streptomyces plasmids from which additional functional Streptomyces replicons can be obtained. Those skilled in the art recognize that all or part of the plasmids may be used to construct vectors exemplifying the present invention so long as the replicon function is not disrupted. the plasmid-containing host and depository accession number are also listed in Table 1.

TABLE 1

| Streptomyces Plasmids | | |
|---|---|---|
| Plasmid | Host | Accession Number |
| SCP2 | *Streptomyces coelicolor* A3 (2) | NRRL* 15042 |
| SCP2* | *Streptomyces coelicolor* M110 | NRRL 15041 |
| pEL7 | *Streptomyces ambofaciens*/pEL7 | NRRL 12523 |

TABLE 1-continued

| Streptomyces Plasmids | | |
|---|---|---|
| Plasmid | Host | Accession Number |
| pUC6 | *Streptomyces espinosus* | NRRL 11439 |
| pUC3 | *Streptomyces* 3022A | NRRL 11441 |
| SLP1 | *Streptomyces lividans* | NCIB** 11417 |
| pNM100 | *Streptomyces virginiae* | NRRL 15156 |
| pEL103 | *Streptomyces granuloruber* A39912.13/pEL103 | NRRL 12549 |

*Agricultural Research Culture Collection (NRRL), 1815 North University Street, Peoria, Illinois, 61604, United States of America

National Collection of Industrial Bacteria (NCIB). Torry Research Station, Post Office Box 31, 135 Abbey Road, Aberdeen AB98DG, Scotland, United Kingdom Phage $\phi$C31 is a well-known Streptomyces phage that is an excellent source of starting material for constructing integrative tylosin resistance-conferring vectors that further exemplify the present invention. A derivative of phage $\phi$C31, phasmid pKC331, is especially preferred for constructing such integrating vectors and can be obtained from E. coli K12 BE447/pKC331, a strain deposited and made part of the permanent stock culture collection of the aforementioned Northern Regional Research Laboratory under the accession number NRRL B-15828. Ligation of the ~37 kb PstI restriction fragment of phasmid pKC331 to the ~3.8 kb tylosin resistance-conferring PstI restriction fragment of plasmid pSVB2 results in the derivative phages pSVB3310 and pSVB3311. These phages are integrative vectors which confer tylosin resistance to Streptomyces and thus further exemplify the present invention. Restriction site and function maps of phages pSVB3310 and pSVB3311 are respectively presented in FIGS. 9 and 10** of the accompanying drawings.

The vectors of the present invention comprise a Streptomyces replicon and a tylosin resistance-conferring restriction fragment. Because amplification and manipulation of plasmids is done faster and more efficiently in E. coli than in Streptomyces, it is convenient to add DNA sequences that also allow for replication in E. coli. Thus, the additions of functional replicon-containing and antibiotic resistance-conferring restriction fragments from E. coli plasmids such as, for example, pBR322, pACYC184, pBR325, pBR328 and the like are highly advantageous and add to the general utility of the present illustrative vectors.

The vectors used in the present method confer tylosin resistance to tylosin-sensitive Streptomyces or related host cells. Although 10 $\mu$g/ml of tylosin is generally toxic to tylosin-sensitive Streptomyces, vectors of the present invention confer resistance to levels approaching 10 mg/ml of tylosin. The preferred tylosin concentration for purposes of selection, however, is about 50 $\mu$g/ml for Streptomyces griseofuscus and 500 $\mu$g/ml for S. lividans. The preferred tylosin concentration for purposes of selection for other Streptomyces species is readily determined by procedures well-known in the art. While all embodiments of the present invention are useful, some of the recombinant DNA cloning vectors and transformants are preferred. Accordingly, preferred vectors and transformants are listed in Table 2.

TABLE 2

| Preferred Vectors and Transformants | |
|---|---|
| Vector | Transformant |
| pSVB2 | *Streptomyces lividans* |
| pSVB2 | *Streptomyces griseofuscus* |
| pSVB12 | *Streptomyces lividans* |

TABLE 2-continued

| Preferred Vectors and Transformants | |
|---|---|
| Vector | Transformant |
| pSVB12 | *Streptomyces griseofuscus* |
| pSVB23 | *Streptomyces lividans* |
| pSVB23 | *Streptomyces griseofuscus* |
| pSVB16 | *Streptomyces lividans* |
| pSVB16 | *Streptomyces griseofuscus* |
| pSVB18 | *Streptomyces lividans* |
| pSVB18 | *Streptomyces griseofuscus* |
| pSVB20 | *Streptomyces lividans* |
| pSVB20 | *Streptomyces griseofuscus* |
| pSVB22 | *Streptomyces lividans* |
| pSVB22 | *Streptomyces griseofuscus* |

The method and recombinant DNA cloning vectors of the present invention are not limited for use in a single species or strain of Streptomyces. To the contrary, the method and the vectors are broadly applicable and can be used with tylosin-sensitive host cells of many Streptomyces taxa, particularly restrictionless strains of economically important taxa that produce antibiotics such as aminoglycoside, macrolide, β-lactam, polyether and glycopeptide antibiotics. Such restrictionless strains are readily selected and isolated from Streptomyces taxa by conventional procedures well-known in the art (Lomovskaya et al., 1980, Microbiological Reviews 44:206). Host cells of restrictionless strains lack restriction enzymes and, therefore, do not cut or degrade plasmid DNA upon transformation. For purposes of the present application, host cells containing restriction enzymes that do not cut any of the restriction sites of the present vectors are also considered restrictionless.

Preferred host cells of restrictionless strains of tylosin-sensitive Streptomyces taxa that produce aminoglycoside antibiotics, and in which the present method is especially useful and the present vectors can be transformed, include restrictionless cells of, for example: S. kanamyceticus (kanamycins), S. chrestomyceticus (aminosidine), S. griseoflavus (antibiotic MA 1267), S. microsporeus (antibiotic SF-767), S, ribosidificus (antibiotic SF733), S. flavopersicus (spectinomycin), S. spectabilis (actinospectacin), S. rimosus forma paromomycinus (paromomycins, catenulin), S. fradiae var. italicus (aminosidine), S. bluensis var. bluensis (bluensomycin), S. catenulae (catenulin), S. olivoreticuli var. cellulophilus (destomycin A), S. lavendulae (neomycin), S. albogriseolus (neomycins), S. tenebrarius (tobramycin, apramycin), S. albus var. metamycinus (metamycin), S. hygroscopicus var. sagamiensis (spectinomycin), S. bikiniensis (streptomycin), S. griseus (streptomycin), S. erythrochromogenes var. narutoensis (streptomycin), S. poolensis (streptomycin), S. galbus (streptomycin), S. rameus (streptomycin), S. olivaceus (streptomycin), S. mashuensis (streptomycin), S. hygroscopicus var. limoneus (validamycins), S. rimofaciens (destomycins), S. hygroscopicus forma glebosus (glebomycin), S. fradiae (hybrimycins neomycins), S. eurocidicus (antibiotic A16316C), S. aquacanus (N-methyl hygromycin B), S. crystallinus (hygromycin A), S. noboritoensis (hygromycin), S. hygroscopicus (hygromycins), S. atrofaciens (hygromycin), S. kasugaspinus (kasugamycins), S. kasugaensis (kasugamycins), S. netropsis (antibiotic LL-AM31), S. lividus (lividomycins), S. hofuensis (seldomycin complex) and S. canus (ribosyl paromamine).

Preferred host cells of restrictionless strains of tylosin-sensitive Streptomyces taxa that produce macrolide antibiotics, and in which the present method is especially useful and the present vectors can be transformed, include restrictionless cells of, for example: S. caelestis (antibiotic M188), S. platensis (platenomycin), S. rochei var. volubilis (antibiotic T2636), S. venezuelae (methylmycins), S. griseofuscus (bundlin), S. narbonensis (josamycin, narbomycin), S. fungicidicus (antibiotic NA181), S. griseofaciens (antibiotic PA133A, B), S. roseocitreus (albocycline), S. bruneogriseus (albocycline), S, roseochromogenes (albocycline), S. cinerochromogenes (cineromycin B), S. albus (albomycetin), S. felleus (argomycin, picromycin), S. rochei (lankacidin, borrelidin), S. violaceoniger (lankacidin), S. griseus (borrelidin), S. maizeus (ingramycin), S. albus var. coilmyceticus (coleimycin), S. mycarofaciens (acetylleukomycin, espinomycin) S. griseospiralis (relomycin), S. lavendulae (aldgamycin), S. rimosus (neutramycin), S. deltae (deltamycins), S. fungicidicus var. espinomyceticus (espinomycins), S. furdicidicus (mydecamycin), S. ambofaciens (spiramycin, foromacidin D), S. eurocidicus (methymycin), S. griseolus (griseomycin), S. flavochromogenes (amaromycin, shincomycins), S. fimbriatus (amaromycin), S. fasciculus (amaromycin), S. erythreus (erythromycins), S. antibioticus (oleandomycin), S. olivochromogenes (oleandomycin), S. spinichromogenes var. suragaoenesis (kujimycins), S. kitasatoensis (leucomycin), S. narbonensis var. josamyceticus (leucomycin A3, josamycin), S. albogriseolus (mikonomycin), S. bikiniensis (chalcomycin), S. cirratus (cirramycin), S. djakartensis (niddamycin), S. eurythermus (angolamycin), S. goshikiensis (bandamycin), S. griseoflavus (acumycin), S. halstedii (carbomycin), S. tendae (carbomycin), S. macrosporeus (carbomycin), S. thermotolerans (carbomycin), and S. albireticuli (carbomycin).

Preferred host cells of restrictionless strains of tylosin-sensitive Streptomyces taxa that produce β-lactam antibiotics, and in which the present method is especially useful and the present vectors can be transformed, include restrictionless cells of, for example: S. lipmanii (A16884, MM4550, MM13902), S. clavuligerus (A16886B, clavulanic acid), S. lactamdurans (cephamycin C), S. griseus (cephamycin A, B), S. hygroscopicus (deacetoxycephalosporin C), S. wadayamensis (WS-3442D), S. chartreusis (SF 1623), S. heteromorphus and S. panayensis (C2081X); S. cinnamonensis, S. fimbriatus, S. halstedii, S. rochei and S. viridochromogenes (cephamycins A, B); S. cattleya (thienamycin); and S. olivaceus, S. flavovirens, S. flavus, S. fulvoviridis, S. argenteolus and S. sioyaensis (MM 4550 and MM 13902).

Preferred host cells of restrictionless strains of tylosin-sensitive Streptomyces taxa that produce polyether antibiotics, and in which the present method is especially useful and the present vectors can be transformed, include restrictionless cells of, for example: S. albus (A204, A28695A and B, salinomycin), S. hygroscopicus (A218, emericid, DE3936), A120A, A28695A and B, etheromycin, dianemycin), S. griseus (grisorixin), S. conglobatus (ionomycin), S. eurocidicus var. asterocidicus (laidlomycin), S. lasaliensis (lasalocid), S. ribosidificus (lonomycin), S. cacaoi var. asoensis (lysocellin), S. cinnamonensis (monensin), S. aureofaciens (narasin), S. gallinarius (RP 30504), S. longwoodenis (lysocellin), S. faveolus (CP38936), S. mutabilis (S-11743a) and S. violaceoniger (nigericin).

Preferred host cells of restrictionless strains of tylosin-sensitive Streptomyces taxa or related genera such as, for example. Nocardia that produce glycopeptide antibiotics, and in which the present method is especially useful and the present vectors can be transformed, include restrctionless cells of, for example: Nocardia orientalis and S. haranomachiensis (vancomycin); Nocardia candidus (A-35512, avoparcin), S. eburosporeus (LL-AM 374), S. virginiae (A41030) and S. toyocaensis (A47934).

Preferred host cells of restrictionless strains of tylosin-sensitive Streptomyces taxa, and in which the present method is especially useful and the present vectors can be transformed, include restrictionless cells of, for example: S. coelicolor, S. granuloruber, S. roseosporus, S. lividans, S. tenebrarius, S. acrimycins, S. glaucescens, S. parvilin, S. pristinaespiralis, S. violaceoruber, S. vinaceus, S. espinosus, S. azureus, S. griseofuscus, S. fradiae, S. ambofaciens and S. toyocaensis.

The method and recombinant DNA cloning vectors of the present invention have broad utility and help fill the need for suitable cloning vehicles for use in Streptomyces and related organisms. Moreover, the ability of the present vectors to confer tylosin resistance provides a functional means for selecting transformants. This is important because of the practical necessity for determining and selecting the particular cells that have acquired vector DNA.

Additional DNA segments, that lack functional tests for their presence, can also be inserted onto the present vectors, and then transformants containing the non-selectable DNA can be isolated by tylosin selection. Such non-selectable DNA segments can be inserted at any site, except within regions necessary for plasmid function and replication or within the tylosin resistance-conferring gene, and include, but are not limited to, genes that specify antibiotic modification enzymes and regulatory genes of all types.

More particularly, a non-selectable DNA segment that comprises a gene is inserted on a plasmid such as, for example, plasmid pSVB2 at the central ClaI restriction site of the thiostrepton resistance gene. Such an insertion inactivates the thiostrepton resistance gene and thus allows for the easy identification of transformants containing the recombinant plasmid. This is done by first selecting for tylosin resistance and, secondarily, identifying those tylosin-resistant transformants that are not resistant to thiostrepton. Therefore, the ability to select for tylosin resistance in Streptomyces and related cells allows for the efficient isolation of the extremely rare cells that contain the particular non-selectable DNA of interest.

The functional test for tylosin resistance, as described herein above, is also used to locate DNA segments that act as control elements and direct expression of an individual antibiotic resistance-conferring gene. Such segments, including, but not limited to, promoters, attenuators, repressor and inducer binding-sites, ribosomal binding-sites and the like, are used to control the expression of other genes in cells of Streptomyces and related organisms.

The tylosin resistance-conferring vectors of the present invention are also useful for ensuring that linked DNA elements are stably maintained in host cells over many generations. These genes or DNA fragments, covalently linked to the tylosin resistance-conferring restriction fragment and propagated in Streptomyces, are maintained by exposing the transformants to levels of tylosin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The method, cloning vectors and transformants of the present invention provide for the cloning of genes to improve yields of various products that are currently produced in Streptomyces and related cells. Examples of such products include, but are not limited to, Streptomycin, Cephalosporins, Actaplanin, Apramycin, Narasin, Monensin, Tobramycin, Erythromycin and the like. The present invention also provides selectable vectors that are useful for cloning, characterizing and reconstructing DNA sequences that code: for commercially important proteins such as, for example, human insulin, human proinsulin, glucagon, interferon and the like; for enzymatic functions in metabolic pathways leading to commercially important processes and compounds; or for control elements that improve gene expression. These desired DNA sequences also include, but are not limited to, DNA that codes for enzymes that catalyze synthesis of derivatized antibiotics such as, for example, Streptomycin, Cephalosporin, Apramycin, Actaplanin, Narasin, Tobramycin, Monensin and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

Streptomyces can be cultured in a number of ways using any of several different media. Carbohydrate sources which are preferred in a culture medium include, for example, molasses, glucose, dextrin and glycerol. Nitrogen sources include, for example, soy flour, amino acid mixtures and peptones. Nutrient inorganic salts are also incorporated and include the customary salts capable of yielding sodium, potassium, ammonium, calcium, phosphate, chloride, sulfate and the like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and detail the invention disclosed herein. Both an explanation of and the actual procedures for constructing the invention are described where appropriate.

EXAMPLE 1

Isolation of Plasmid pSVB2

A. Culture of Streptomyces lividans TK23/pSVB2

Figure 1:
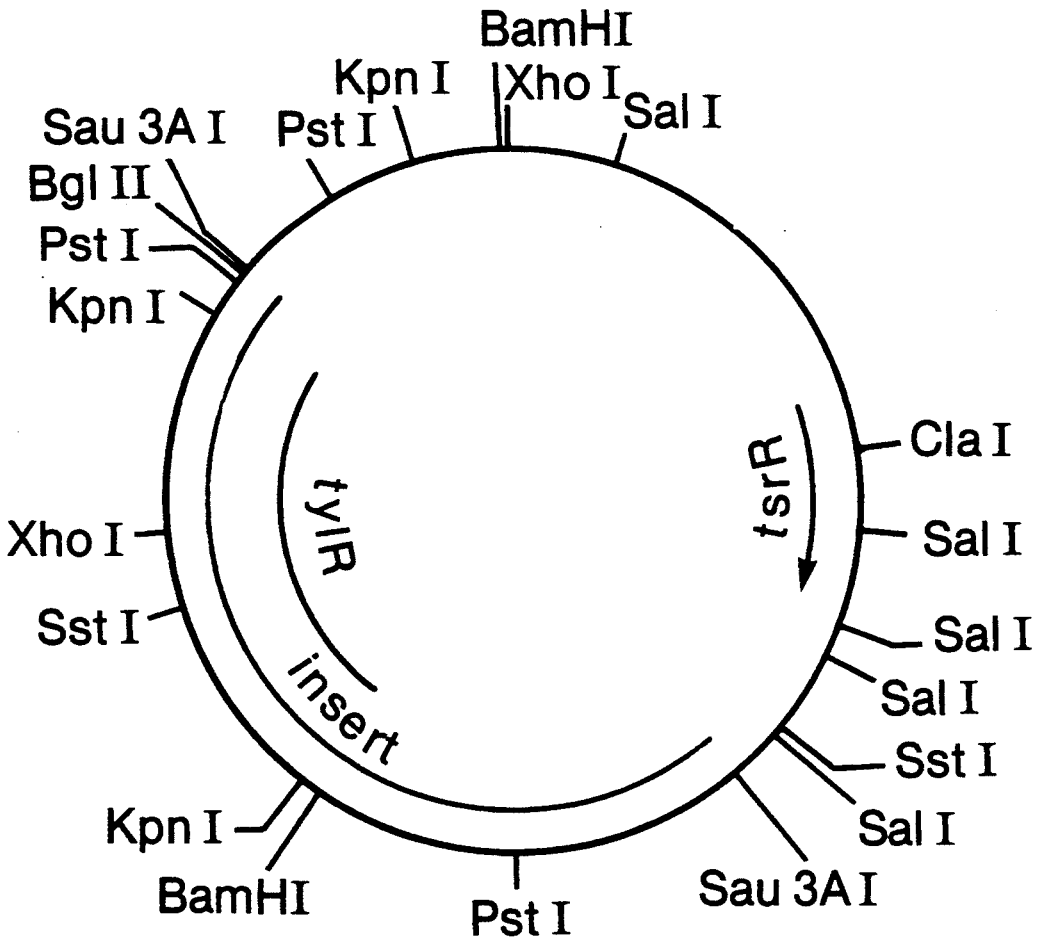
FIG. 1 shows the restriction site and function map of plasmid pSVB2.
Figure 2:
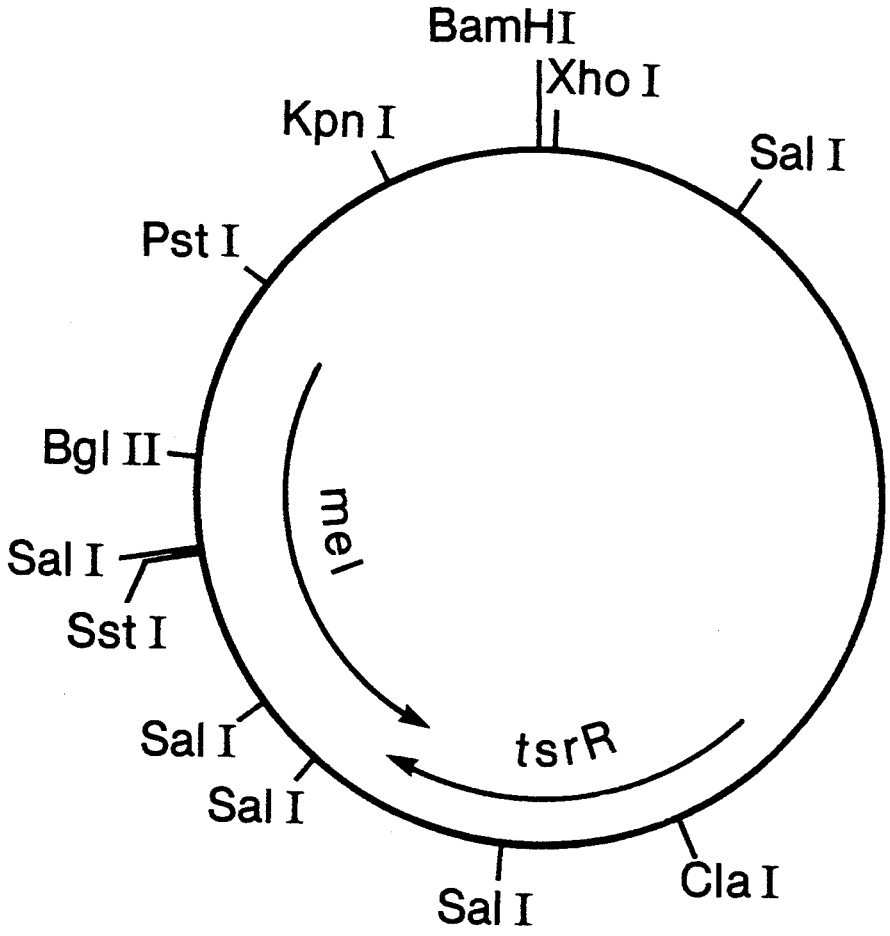
FIG. 2 shows the restriction site and function map of plasmid pIJ702.

About $10^8$ spores of Streptomyces lividans TK23/pSVB2 (NRRL 15880) were inoculated into 10 ml of TSB medium (Trypticase Soy Broth*) containing 10 μg/ml thiostrepton and grown at 29° C. until the culture was in early stationary phase. The culture was then homogenized, and 5 ml of the homogenized culture were used to inoculate 100 ml of TSB also containing thiostrepton. The 100 ml of culture were incubated at 29° C. until the Streptomyces lividans TK23/pSVB2 cells reached stationary phase.

*TSB is made at 30 g/l and is obtained from: Bethesda Research Laboratories, Inc., 8717 Grovemont Circle, P.O. Box 577, Gaithersburg, Md. 20760.

B. Plasmid Isolation

The cells were collected and washed once with a 10.3% sucrose solution. The cells were then suspended in 24 ml of 10.3% sucrose, and 6 ml of 5X lysozyme solution (125 mM Tris-HCl, pH=8; 125 mM $Na_2$ EDTA, pH=8; 10 mg/ml lysozyme; and 10.3% sucrose) were added. After mixing and then incubating at 30° C. for 30–60 minutes, about 18 ml of a solution that was 0.3M NaOH, 1% SDS and prewarmed to 50° C. were added, mixed and the resultant mixture incubated at 80° C. for 10 minutes. The mixture was then cooled to room temperature, and 12 ml of a solution made by mixing 500 g phenol, 500 g $CHCl_3$ and 0.5 g 8-hydroxyquinoline in 200 ml $H_2O$ were added and mixed well with the cell-extract. The phases were separated by centrifugation at 6000–8000 rpm for 10 minutes; approximately 45 ml of the resulting supernatant were transferred to a clean bottle.

Next, 4.5 ml of 3M NaOAc and 50 ml of isopropanol were added to the supernatant, and the solution was mixed and left at room temperature for 30 minutes. The solution was then centrifuged (8000 rpm for 30 minutes) and the resulting supernatant discarded. The pellet was resuspended in 7.5 ml TE buffer (10 mM Tris-HCl, pH=8 and 1 mM EDTA) containing 8 g CsCl. After adding 0.5 ml of a 10 mg/ml solution of ethidium bromide, the solution was centrifuged at 40,000 rpm for 48 hours at 20° C. The resulting plasmid band was extracted 3–5 times with isopropanol saturated with TE buffer and CsCl. After the extractions, the sample was diluted with four volumes TE buffer and then 2.5 times the final volume of ethanol added. The resulting solution was mixed and incubated overnight at −20° C.

The precipitate resulting from the overnight incubation at −20° C. was collected by centrifugation (10,000 rpm for 30 minutes), dried and reprecipitated twice. The precipitations were done by suspending the pellet in TE buffer, adding NaOAc to 0.3M, adding 2.5 volumes ethanol, chilling at −70° C. for 10–15 minutes and then centrifuging the solution as above. The procedure yielded about 100 μg of plasmid pSVB2 DNA, which was suspended in TE buffer at a concentration of 1 μg/μl and stored at 4° C.

EXAMPLE 2

Isolation of Plasmid pIJ702

Streptomyces lividans/pIJ702 (ATCC 39155) was cultured and plasmid pIJ702 isolated in substantial accordance with the teaching of Example 1. Thiostrepton selection (10 μg/ml) was used to ensure plasmid pIJ702 maintenance. The ~100 μg of plasmid pIJ702 DNA obtained was suspended in 1 ml of TE and stored at 4° C.

EXAMPLE 3

Construction of Plasmids pSVB12 and pSVB23

A. KpnI Digestion of Plasmid pSVB2 and Purification of the ~2.6 kb KpnI Restriction Fragment Approximately 50 μg (50 μl) of the plasmid pSVB2 DNA isolated in Example 1 were mixed with 10 μl 10X KpnI buffer*, 5 μl (50 units) restriction enzyme KpnI and 35 μl $H_2O$ and reacted at 37° C. for two hours. After heat inactivation, the reaction mixture was loaded into an agarose gel and the desired ~2.6 kb KpnI restriction fragment purified in substantial accordance with the teaching of Maniatis et al., 1982, Molecular Cloning, pp. 164–166. The approximately 10 μg of the tylosin resistance gene-containing ~2.6 kb KpnI restriction fragment obtained was suspended in 100 μl of TE buffer and stored at 4° C.

*10X KpnI buffer composition is:

60 mM NaCl
60 mM Tris-HCl, pH=7.5
60 mM $MgCl_2$
60 mM 2-mercaptoethanol
1 mg/ml BSA

B. Preparation of KpnI-Digested Plasmid pIJ702

Approximately 1 μg (10 μl) of the plasmid pIJ702 DNA isolated in Example 2 was mixed with 5 μl 10X KpnI buffer, 2 μl restriction enzyme KpnI (10 Units) and 33 μl $H_2O$ and reacted at 37° C. for two hours. After heat inactivation at 65° C. for 10 minutes, the digested plasmid DNA was stored at −20° C.

C. Ligation of Fragments to Form Plasmids pSVB12 and pSVB23

Figure 3:
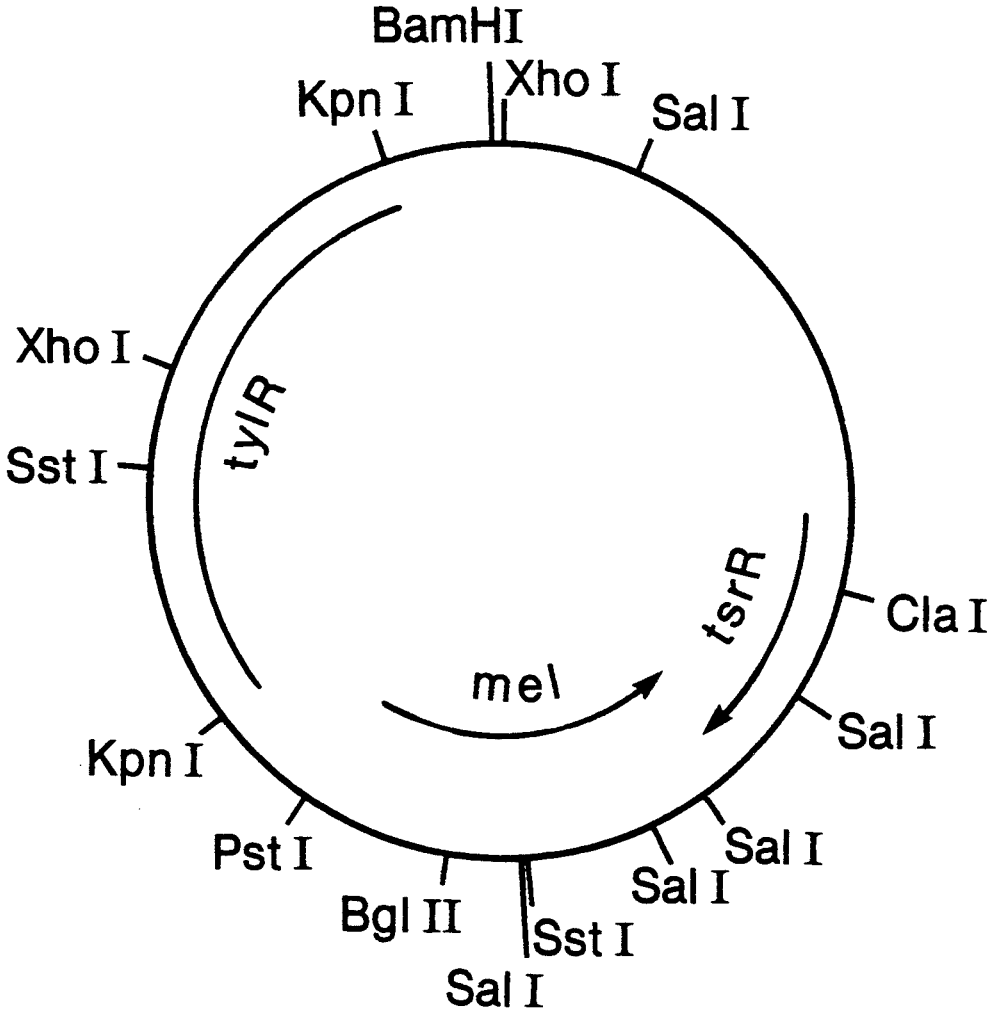
FIG. 3 shows the restriction site and function map of plasmid pSVB12.
Figure 4:
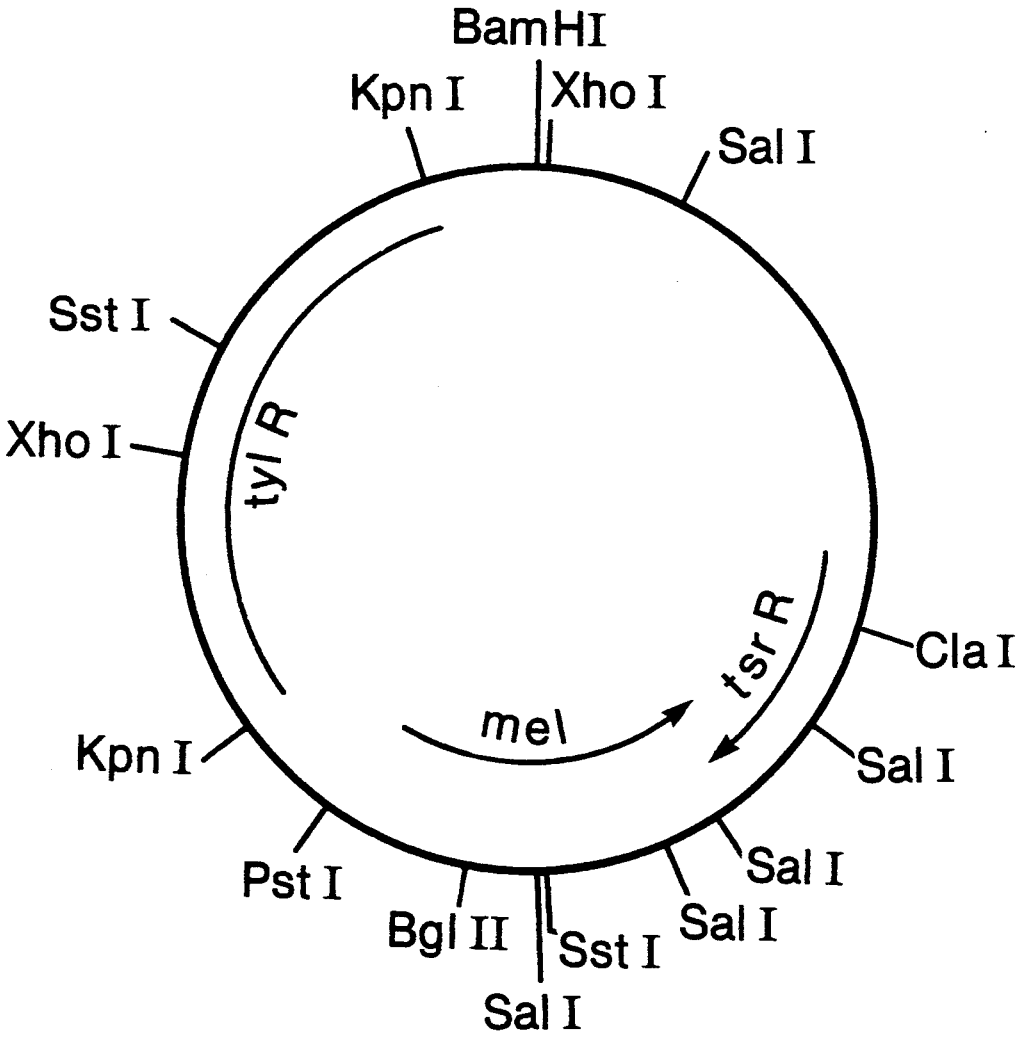
FIG. 4 shows the restriction site and function map of plasmid pSVB23.

Five μl of the ~2.6 kb KpnI restriction fragment prepared in Example 3A were mixed with 25 μl of the KpnI-digested plasmid pIJ702 in Example 3B and then precipitated by adding 3 μl of 3M NaOAc and 75 μl of ethanol, chilling at −70° C. for 30 minutes and centrifuging. The resultant DNA pellet was suspended in 39 μl of 1X Ligase buffer* and 1 μl T4 DNA Ligase and incubated overnight at 16° C. The ligated DNA constituted the desired plasmids pSVB12 and pSVB23. The plasmids differ only in respect to the orientation of the ~2.6 kb KpnI restriction fragment (see FIGS. 3 and 4).

*1X Ligase buffer composition is:

50 mM Tris-HCl, pH=7.8
10 mM $MgCl_2$
20 mM dithiothreitol
1 mM ATP
50 μg/ml BSA

EXAMPLE 4

Construction of Plasmids pSVB16 and pSVB18

A. PstI Digestion of Plasmid pSVB2 and Purification of the ~3.8 kb PstI Restriction Fragment Approximately 50 μg (50 μl) of the plasmid pSVB2 DNA isolated in Example 1 were mixed with 10 μl 10X PstI buffer*, 5 μl restriction enzyme PstI and 35 μl $H_2O$ and reacted at 37° C. for two hours. The desired ~3.8 kb tylosin resistance gene-containing PstI restriction fragment was purified in substantial accordance with the teaching of Maniatis et al., 1982, and the ~10 μg of purified fragment obtained was suspended in 100 μl of TE buffer and stored at 4° C.

*10X PstI buffer composition is:

1M NaCl
100 mM Tris-HCl, pH=7.5
100 mM $MgCl_2$
1 mg/ml BSA

B. PstI Digestion of Plasmid pIJ702

Approximately 1 μg (10 μl) of the plasmid pIJ702 isolated in Example 2 were mixed with 5 μl 10X PstI buffer, 2 μl (~10 Units) restriction enzyme PstI and 33 μl $H_2O$ and reacted at 37° C. for two hours. The reaction was stopped by heating at 65° C. for 10 minutes, and the PstI-digested DNA was then stored at −20° C.

C. Ligation of Fragments to Form Plasmids pSVB16 and pSVB18

Figure 5:
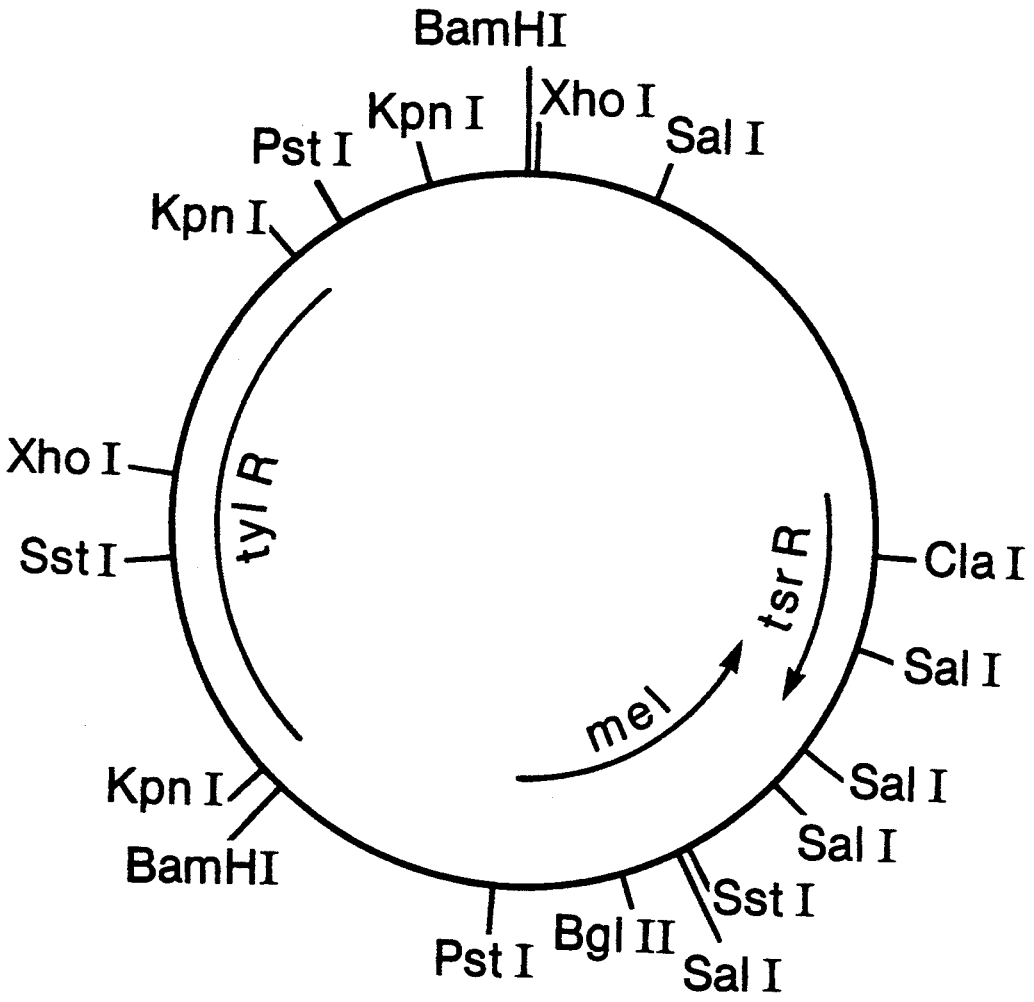
FIG. 5 shows the restriction site and function map of plasmid pSVB16.
Figure 6:
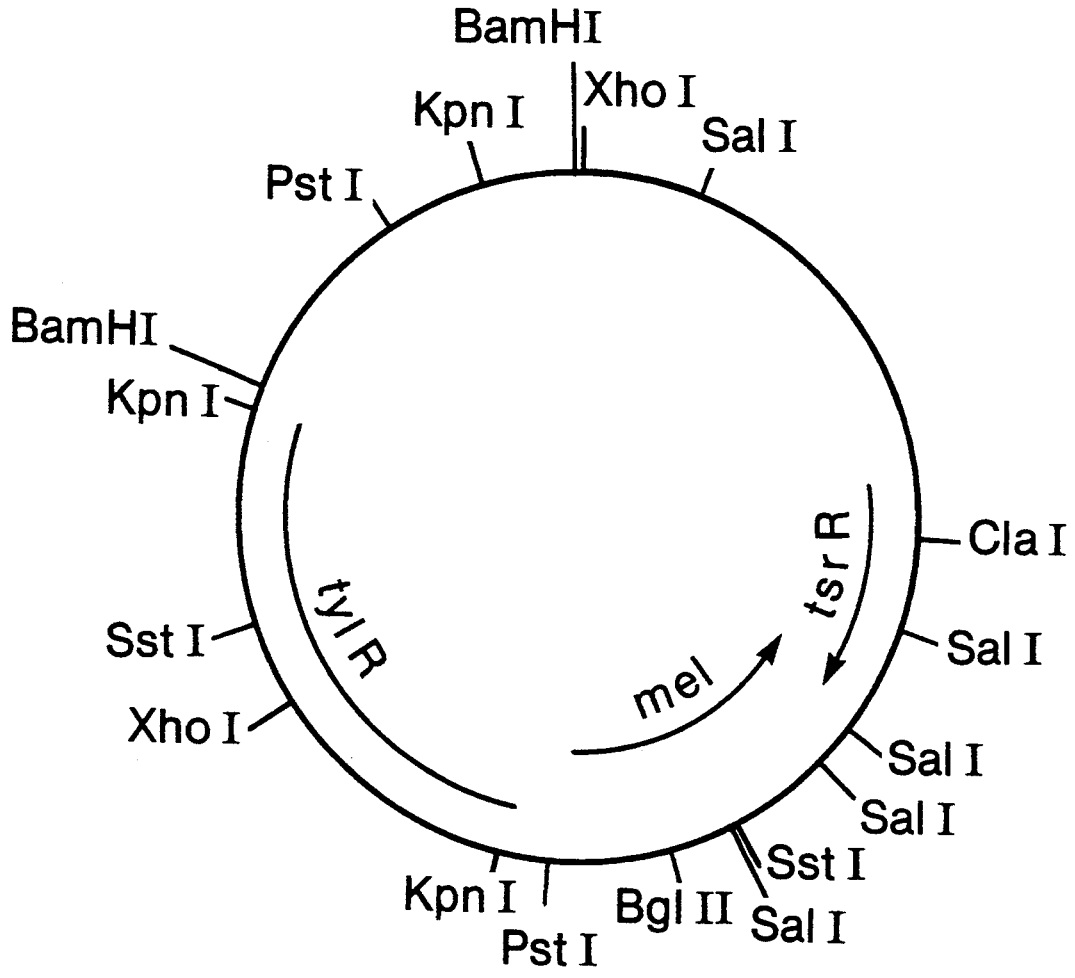
FIG. 6 shows the restriction site and function map of plasmid pSVB18.

Five μl of the ~3.8 kg tylosin resistance gene-containing PstI restriction fragment isolated in Example 4A and 25 μl of the PstI-digested plasmid pIJ702 isolated in Example 4B were ligated in substantial accordance with the teaching of Example 3C. The ligated DNA constituted the desired plasmids pSVB16 and pSVB18. The plasmids differ only in respect to the orientation of the ~3.8 kb PstI restriction fragment (see FIGS. 5 and 6).

EXAMPLE 5

Construction of Plasmids pSVB20 and pSVB22

A. BamHI and BglII Digestion of Plasmid pSVB2 and Isolation of the ~2.9 kb BamHI-BglII Restriction Fragment Approximately 50 μg (50 82 l) of the plasmid pSVB2 isolated in Example 1 were mixed with 10 μl 10X BamHI-BglII buffer*, 5 μl (~50 Units) restriction enzyme BamHI, 5 μl (~50 Units) restriction enzyme BglII and 30 μl $H_2O$ and reacted at 37° C. for two hours. After heat inactivation, the desired ~2.9 kb BamHI-BglII restriction fragment containing the tylosin resistance gene was purified in substantial accordance with the teaching of Maniatis et al., 1982, and the ~10 μg of purified fragment obtained was suspended in 100 μl of TE buffer and stored at 4° C.

*10X BamHI-BglII buffer composition is:

1.25M NaCl
80 mM Tris. HCl, pH=7.7
80 mM $MgCl_2$
100 mM 2-mercaptoethanol
1 mg/ml BSA

B. BglII Digestion of Plasmid pIJ702

Approximately 1 μg (10 μl) of the plasmid pIJ702 DNA isolated in Example 2 were mixed with 5 μl 10X BglII buffer*, 2 μl (20 units) restriction enzyme BglII and 33 μl $H_2O$ and reacted at 37° C. for two hours. After inactivating the reaction at 65° C. for 10 minutes, the BglII-digested plasmid DNA was stored at −20° C.

*10X BglII buffer composition is:

1M NaCl
100 mM Tris-HCl, pH=7.4
100 mM $MgCl_2$
100 mM 2-mercaptoethanol
1 mg/ml BSA

C. Ligation of Fragments to Form Plasmids pSVB20 and pSVB22

Figure 7:
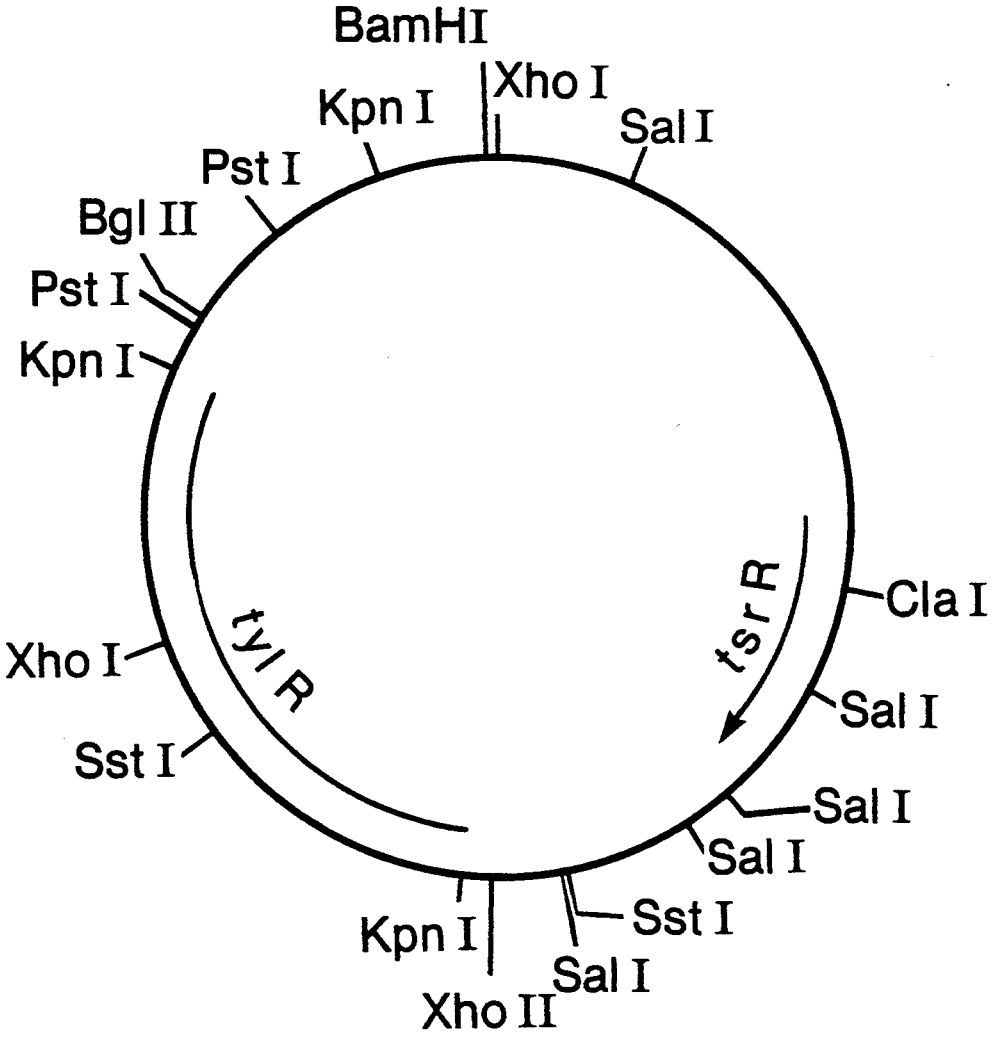
FIG. 7 shows the restriction site and function map of plasmid pSVB20.
Figure 8:
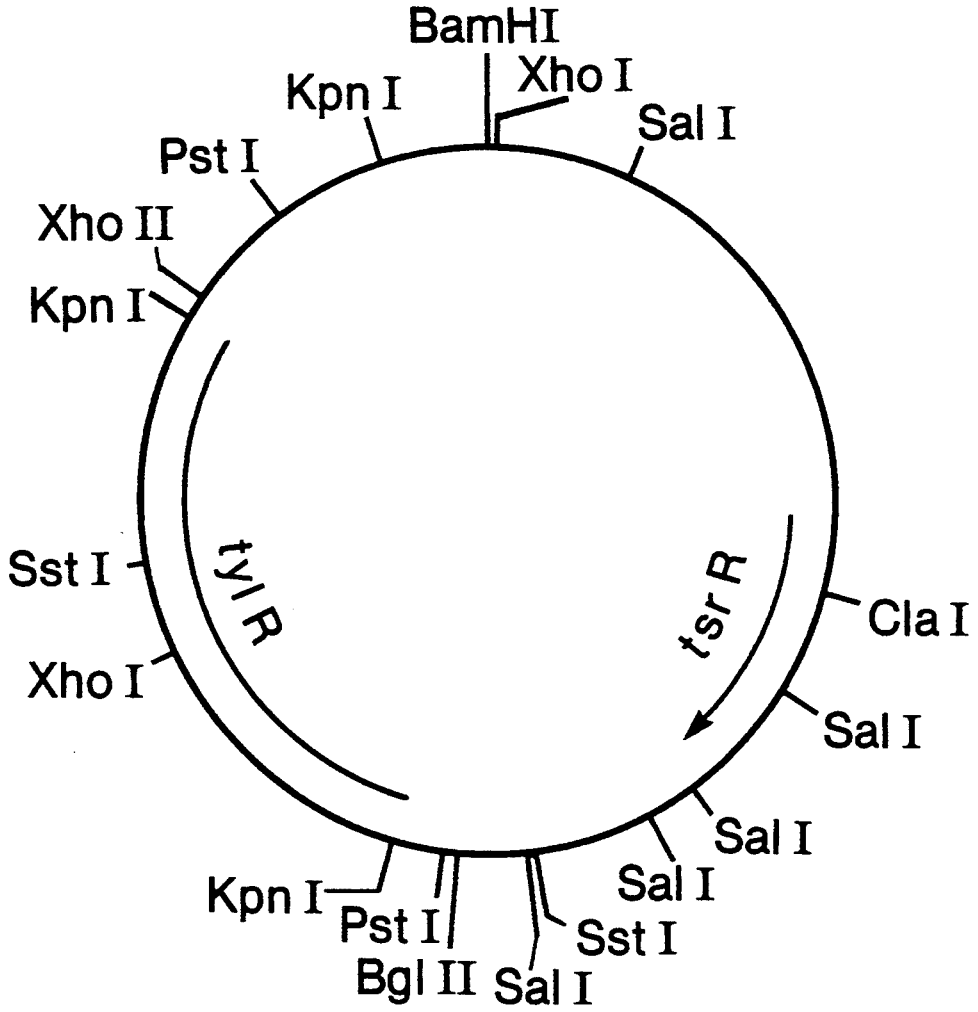
FIG. 8 shows the restriction site and function map of plasmid pSVB22.

Five μl of the ~2.9 kb BamHI-BglII restriction fragment containing the tylosin resistance-conferring gene isolated in Example 5A were mixed with 25 μl of the BglII-digested plasmid pIJ702 prepared in Example 5B and then ligated in substantial accordance with the teaching of Example 3C. The ligated DNA constituted the desired plasmids pSVB20 and pSVB22 (see FIGS. 7 and 8). Note that when a BamHI and BglII site are ligated together, an XhoII recognition sequence is formed. Plasmids pSVB20 and pSVB22 differ only in respect to the orientation of the inserted ~2.9 kb BamHI-BglII restriction fragment.

EXAMPLE 6

Construction of Tylosin-Resistant Streptomyces griseofuscus Transformants

A. List of Solutions

The following solutions are referred to throughout Examples 6 and 7 and are presented here for clarity.

| Ingredient | Amount |
|---|---|
| 1. P medium (~100 ml): | |
| Sucrose | 10.3 g |
| $K_2SO_4$ | 0.025 g |
| Trace element solution (see #3) | 0.2 ml |
| $MgCl_2.6H_2O$ | 0.203 g |
| Water to | 80 ml |
| After autoclaving add: | |
| $KH_2PO_4$ (0.5%) | 1 ml |
| $CaCl_2.2H_2O$ (3.68%) | 10 ml |
| (N-tris (hydroxymethyl)-methyl-2-aminoethane sulphonic acid) "TES" buffer, 0.25 M. pH = 7.2 | 10 ml |
| 2. L medium (~100 ml): | |
| Sucrose (10.3%) | 100 ml |
| TES buffer, pH 7.2 (0.25 M) | 10 ml |
| $K_2SO_4$ (2.5%) | 1 ml |
| Trace element solution (see #3) | 0.2 ml |
| $KH_2PO_4$ (0.5%) | 1 ml |
| $MgCl_2$ (2.5 M) | 0.1 ml |
| $CaCl_2$ (0.25 M) | 1 ml |
| Lysozyme | 1 mg/ml |

The L medium is filter sterilized after preparation.

| Ingredient | Amount |
|---|---|
| 3. Trace element solution (~1 l): | |
| $ZnCl_2$ | 40 mg |
| $FeCl_3.6H_2O$ | 200 mg |
| $CuCl_2.2H_2O$ | 10 mg |
| $MnCl_2.4H_2O$ | 10 mg |
| $Na_2B_4O_7.10_2O$ | 10 mg |
| $(NH_4)_6Mo_7O_{24}.4H_2O$ | 10 mg |
| 4. R2 Regeneration Medium (~1 l): | |

-continued

| Ingredient | Amount |
|---|---|
| Sucrose | 103 g |
| $K_2SO_4$ | 0.25 g |
| Trace element solution | 2 ml |
| $MgCl_2.6H_2O$ | 10.12 g |
| glucose | 10 g |
| L-asparagine.$1H_2O$ | 2.0 g |
| casamino acids | 0.1 g |
| Agar | 22 g |
| Water | to 700 ml |
| After autoclaving add: | |
| $KH_2PO_4$ (0.05 g/100 ml) | 100 ml |
| $CaCl_2$ (2.22 g/100 ml) | 100 ml |
| TES Buffer (5.73 g/100 ml, pH = 7.2) | 100 ml |
| NaOH (5N) | 1 ml |
| 5. T medium (~14.5 ml): | |
| Sucrose (10.3%) | 2.5 ml |
| Distilled water | 7.5 ml |
| Trace element solution | 20 μl |
| $K_2SO_4$ (2.5%) | 100 μl |
| $CaCl_2$ (5 M) | 217 μl |
| Tris-maleic acid, pH = 8 (1 M) | 543 μl |
| Polyethylene glycol 1000 | 3.63 g |

All components were sterilized by autoclaving. The liquid components were mixed and then added to the appropriate amount of molten polyethylene glycol. The first four ingredients may be pre-mixed and stored at room temperature for at least one month.

| Ingredient | Amount |
|---|---|
| Soft nutrient agar (SNA, ~1 l): | |
| Difco Bacto Nutrient Broth | 8 g |
| Agar | 5 g |
| 7. R2YE medium is R2 medium with 20 ml of 25% yeast extract added per liter. | |
| 8. Yeast Extract - Malt Extract (YEME, ~1 l): | |
| Yeast extract | 3 g |
| Peptone | 5 g |
| Malt extract | 3 g |
| Glucose | 10 g |
| 9. YEME + 34% Sucrose Liquid Complete Medium is YEME with 340 g/liter of sucrose. | |
| 10. YMX Media (~1 l): | |
| Yeast extract | 3 g |
| Malt extract | 3 g |
| Glucose | 2 g |
| Agar | 20 g |

B. Growth of Cultures for Preparation of Protoplasts

A vegetative inoculum was conventionally prepared by growing Streptomyces griseofuscus C581 (ATCC 23916) under submerged conditions for 20 hours at 30° C. in TSB supplemented with 0.4% glycine. The procedure for protoplasting S. griseofuscus is generally performed as follows. A culture of S. griseofuscus was spread on a plate containing YMX agar (0.3% yeast extract, 0.3% malt extract, 0.2% dextrose and 2% agar) and incubated at 30° C. for approximately 48 hours. A single bacterial colony from the plate was then inoculated into 10 ml TSB; the culture was homogenized and then incubated at 30° C. overnight. About 4 ml of the overnight culture were homogenized, added to 100 ml TSB supplemented with 0.4% glycine and then incubated overnight at 30° C. This procedure was repeated, using the fresh overnight culture. About 50 ml of 50% (v/v) glycerol were then added to the culture and 15 samples were frozen and stored for up to six months at −20° C. The frozen cells were thawed by placing the tube at room temperature is a beaker of water. The cells were then harvested in a bench top centrifuge and washed three times in 10 ml of 10.3% sucrose. The cell pellet was resuspended in 10 ml of P medium supplemented with lysozyme (1 mg/ml) and incubated at 30° C. for 2 hours. The mixture was then centrifuged to pellet the protoplasts. The pellet was washed three times, using 10 ml P medium and vortexing the pellet into solution each wash. The protoplasts were resuspended in 2 ml P medium for subsequent transformation.

C. Transformation

About 10 μl of plasmid DNA in ligation buffer and about 150 μl of Streptomyces griseofuscus protoplasts were mixed together in a test tube, and then 101 μl of 50% PEG 1000 in P medium were added. After a 1–2 minute wait, enough P medium to bring the volume up to 1 ml was added. The transformed cells were plated out on R2 medium and incubated at 30° C. for 7–10 days. Replicaplates were made on YMX media containing 50 μg/ml tylosin to identify transformants. Alternatively, transformants can be directly selected by overlaying the plates, after overnight incubation at 30° C., with soft R2 medium containing enough tylosin to make the final plate concentration of tylosin 50 μg/ml. The resulting tylosin-resistant S. griseofuscus colonies can be isolated according to known procedures, cultured and then conventionally identified as described below. The transformant culture can then be used for subsequent production and isolation of plasmid DNA.

D. Analysis of Streptomyces griseofuscus Transformants

The resultant transformants are cultured on YMX agar supplemented with tylosin (50 μg/ml) to obtain single colonies. These single colonies are used to inoculate 10 ml TSB cultures also containing tylosin (10 μg/ml). The cultures are homogenized and then grown overnight at 30° C. in a rotary shaker.

Plasmid isolation for analysis is done by a small-scale version of the protocol of Example 1; the CsCl gradients of Example 1 are replaced by ethanol precipitations. The mycelium are collected by centrifugation, washed twice with 10.3% sucrose and then suspended in 1–2 ml of 10.3% sucrose. Four hundred μl of the cell mixture are transferred to a small tube, and 100 μl of 5X Lysozyme solution (Example 1) are added. The suspension is incubated at 30° C. for 30–60 minutes, followed by the addition and mixing of 250 μl of 0.3M NaOH containing 1% SDS. The latter solution is kept at 50° C. before its addition to the cell mix. After the cell mixture is placed at 80° C. for 10 minutes and then cooled to room temperature, the sample is extracted with 100 μl of phenol:$CHCl_3$ (50:50). The aqueous phase is transferred to a clean tube, made 0.3 M in NaOAc, and then one volume of isopropanol is added. After holding at room temperature for five minutes, the DNA is pelleted by centrifugation. The pellet is dissolved in 400 μl of TE buffer and made 0.3M in NaOAc. About 2.5 volumes of ethanol are added, followed by chilling at −70° C. for 30 minutes. After centrifugation and another precipitation, the plasmid DNA is suspended in 50 μl of TE buffer. Restriction enzyme cutting and electrophoretic analysis of the reaction products are used to determine plasmid structure.

E. Preparation of Streptomyces griseofuscus/pSVB2, S. griseofuscus/pSVB12, S. griseofuscus/pSVB16, S. griseofuscus/pSVB18, S. griseofuscus/pSVB20, S. griseofuscus/pSVB22 and S. griseofuscus/pSVB23

Each of the above constructions are separately made and analyzed in accordance with the foregoing teaching of this Example.

EXAMPLE 7

Construction of Tylosin-Resistant Streptomyces lividans/pSVB12, S. lividans/pSVB16, S. lividans/pSVB18, S. lividans/pSVB20, S. lividans/pSVB22 and S. lividans/pSVB23

This procedure was used to construct and analyze Streptomyces lividans transformants. Plasmids pSVB12, pSVB16, pSVB18, pSVB20, pSVB22 and pSVB23 are each separately and independently used as the transforming DNA.

A. Preparation and Storage of Protoplasts

Streptomyces lividans TK23 (NRRL 15826) were grown for 40–48 hours at 30° C. in YEME+34% sucrose, 5 mM $MgCl_2$ and 0.5% glycine. The mycelium was recovered by centrifugation (800 g for 10 minutes in a bench top centrifuge) and washed twice in 10.3% sucrose. The mycelium from 25–50 ml of culture was suspended in 3–4 ml of L medium and incubated for 1 hour at 32° C. During this interval the suspension was pipetted up and down once or twice to disperse clumps. Five ml of P medium were added, and the suspension was then filtered through a plug of cotton wool. The protoplasts were recovered by centrifugation (800 g for 10 minutes) and washed twice with 5 ml of P medium. The protoplasts were then suspended in 4 ml of P medium and the number of protoplasts determined microscopically using a hemacytometer slide. If the protoplasts are not to be used immediately, the suspension can be divided into aliquots (about 1 ml) containing $5\times10^9$–$10^{10}$ protoplasts in sterile polypropylene screw-cap tubes. The suspensions were frozen slowly by placing the tubes in a container of ice, which was in turn placed at −70° C. The protoplasts were stored at this temperature until needed. The frozen suspension was thawed rapidly by immersion in a 37° C. water bath prior to use.

B. Protoplast Transformation

Approximately $5\times10^9$ protoplasts were pelleted by centrifugation (800 g for 10 minutes). The supernatant was decanted and the protoplasts were reuspended in the small volume of liquid remaining in the tube. Plasmid DNA in a volume not greater than 20 μl in TE buffer was added, followed immediately by the addition of 0.5 ml of T medium. The mixture was pipetted up and down once or twice to mix the contents. At this point the suspension was either plated directly or diluted with 0.5 ml of P medium and then plated. In either case, about 0.1 ml was inoculated per plate of R2YE medium.

Tylosin-resistant tansformants were selected by replica-plating regenerated protoplasts to R2YE medium containing 500 μg/ml of tylosin. Alternatively, tylosin-resistant transformants can be selected by overlaying the regenerating protoplasts with soft nutrient broth agar containing tylosin. The regeneration plates are incubated for 16–22 hours at 30° C. before the application of 2.5 ml per plate of SNA (45°–50° C.) containing enough tylosin to give a final concentration of 500 μg/ml after diffusion. Melanin production, or lack thereof, by transformants carrying pIJ702 derivatives was detected by incorporating tyrosine at 750 μg/ml into the SNA overlay; those transformants possessing an intact tyrosinase gene become black after growth in the presence of tylosin.

C. Analysis of S. lividans Transformants

The resultant transformants are analyzed in substantial accordance with the teaching of Example 6D.

EXAMPLE 8

Culture of E. coli K12 BE447/pKC331 and Isolation of Phasmid pKC331

A. Culture of E. coli K12 BE447/pKC331

A 2 ml culture of E. coli K12 BE447/pKC331 (NRRL B-15828) was grown in the presence of 50 μg/ml ampicillin in TY media (1% tryptone, 0.5% NaCl and 0.5% yeast extract, pH 7.4) until the cells reached stationary phase. The 2 ml culture was then used to inoculate a flask containing 1 liter of TY media containing 50 μg/ml ampicillin and growth continued until the optical density of the culture at 550 nanometers was between 0.50 and 0.75 absorbance units. When the O.D. 550 reached the 0.50–0.75 range, 1 g of uridine was added, and, 15 minutes later, 170 mg of chloramphenicol phenicol was added. The incubation and culturing was then continued for 16 hours.

B. Isolation of Phasmid pKC331

The culture was centrifuged and the cell pellet resuspended in 10 ml of a solution that was 25% w/v sucrose; 50 mM Tris-HCl, pH=8; and 1 mM EDTA. Next, 2 ml of 0.5M EDTA and 2 ml of a 5 mg/ml lysozyme solution is 0.25M Tris-HCl, pH=8 were added, and the resultant mixture was incubated at room temperature for 15 minutes. After incubation, about 14 ml of a solution that was 50 mM Tris-HCl, pH=8; 6 mM EDTA; and 0.1% Triton X-100 were added. The lysozyme-treated cells were then mixed by inversion.

The lysed cell mix was centrifuged until the cell debris formed a loose pellet. After the cell debris pellet was discarded and the supernatant extracted with buffered (pH=8) phenol, the aqueous phase was made 0.25M in NaCl and two volumes of ethanol were added. The resultant mixture was chilled to −70° C., and the nucleic acid was pelleted by centrifugation. Further centrifugation (45,000 rpm for 16 hours at 20 C.) using cesium chloride gradients with ethidium bromide was carried out to purify the phasmid DNA. The desired phasmid pKC331 DNA was then collected and the ethidium bromide and cesium chloride removed by conventional procedures. The approximately 1 mg of phasmid pKC331 DNA obtained by this procedure was dissolved in 1 ml of TE buffer (10 mM Tris-HCl, pH 8 and 1 mM EDTA) and stored at −20° C.

EXAMPLE 9

Construction of Phage pSVB3310

A. PstI Digestion of phasmid pKC331 and Isolation of the ~37 kb PstI Restriction Fragment About 10 μg (10 μl) of the phasmid pKC331 isolated in Example 8 are added to 10 μl 10X PstI salts, 2 μl restriction enzyme PstI (~10 Units) and 78 μl $H_2O$. After gentle mixing, the digest is allowed to react 2 hours at 37° C. After digestion, the ~37 kb PstI fragment containing the phage $\phi$C31 sequences is purified by conventional electrophoretic gel means. The purified fragment obtained (~5 $\mu$g) is suspended in 5 $\mu$l of TE buffer.

B. Ligation of the ~3.8 kb Tylosin

Resistance-Conferrign PstI Restriction Fragment to the ~37 PstI Restriction Fragment of Phasmid pKC331

Figure 9:
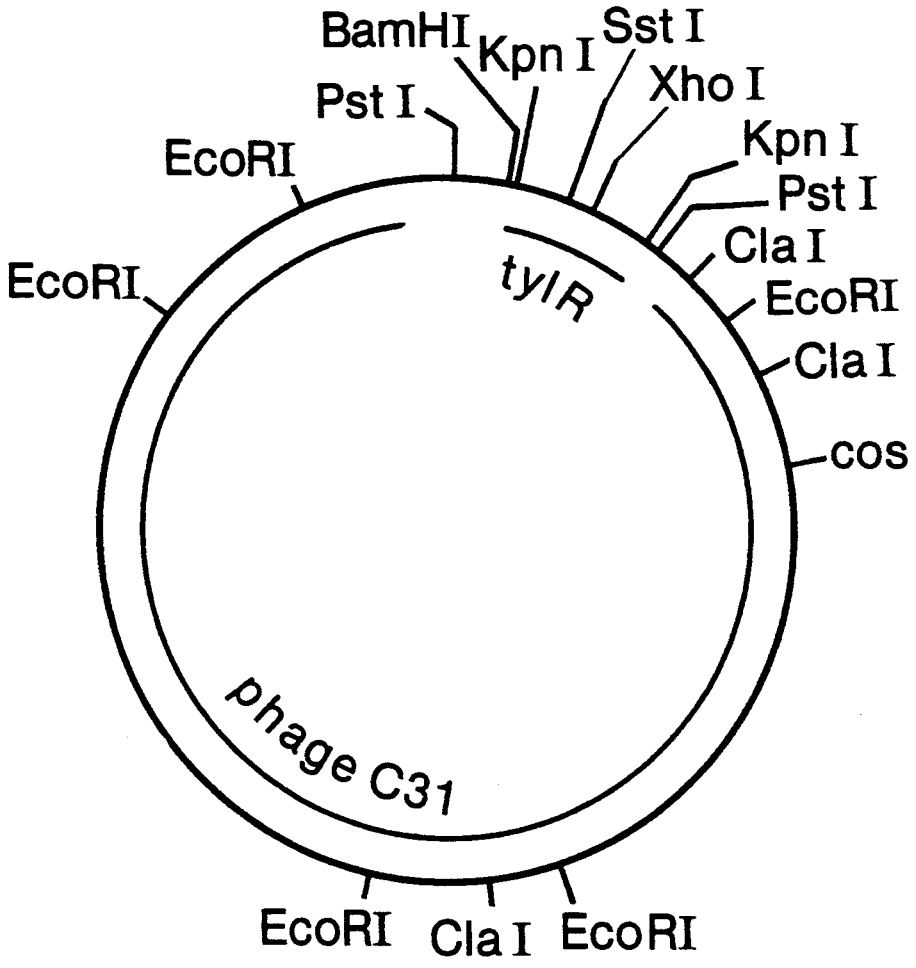
FIG. 9 shows the restriction site and function map of phage pSVB3310.
Figure 10:
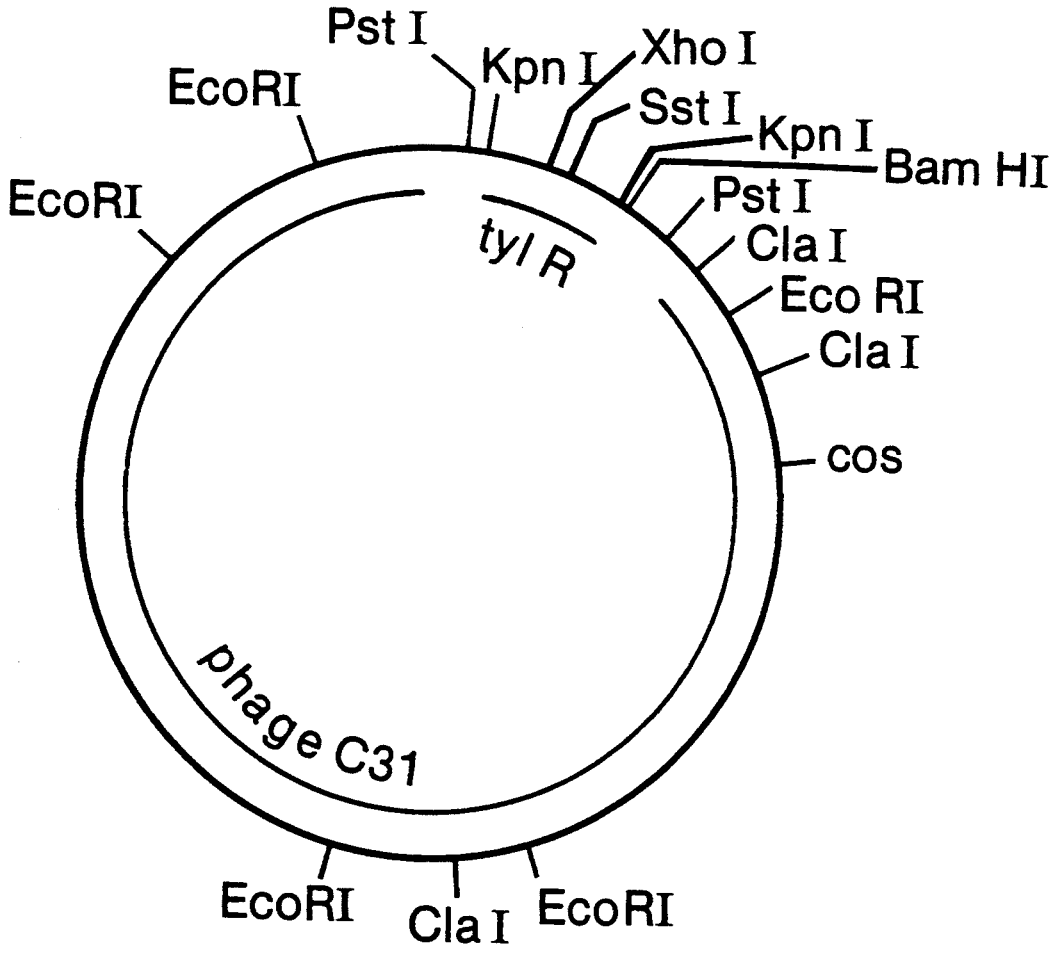
FIG. 10 shows the restriction site and function map of phage pSVB3311.

This ligation is carried out in substantial accordance with the method of Example 3C, except that different restriction fragments are used. In this ligation, 2.5 $\mu$l of the ~37 PstI restriction fragment prepared in Example 9A are ligated to 2 $\mu$l of the fragment obtained in Example 4A to produce the desired phages pSVB3310 and psVB3311. Phage pSVB3311 differs from phage psVB3310 only in respect to the orientation of the ~3.8 kp PstI fragment (see FIGS. 9 and 10). The ligated DNA is used to transform Streptomyces to obtain infective phage particles. The phage particles are then used to prepare tylosin-resistant Streptomyces via chromosomal integration of the vector.

EXAMPLE 10

Construction of Streptomyces lividans/psVB3310

The ligated DNA of Example 9B, 200 $\mu$l of Streptomyces lividans protoplasts, $10^8$ spores of Streptomyces lividans and 500 $\mu$l of 55% polyethylene glycol in P medium are vortexed and alliquots of 25 $\mu$l and 250 $\mu$l are plated onto R2YE plates with 3 ml of R2YE top agar. The plates are incubated at 37° C. Plaques can usually be seen after ~20 hours. After plaques appear, they are removed from the plate and the phage particles washed off the agar into TSB medium. Serial dilutions of the phage suspension are made and aliquots removed and mixed with $10^8$ spores of Streptomyces lividans. These dilutions are made in order to achieve a good plaque distribution on the plate. The mixtures are plated on R2YE plates and incubated at 30° C. until sporulation occurs, a process taking about 4 days. After sporulation, the plates are replica plated onto fresh R2YE plates containing 500 $\mu$g/ml tylosin. The replica plates are then incubated at 30° C. for 3–4 days, and the resultant S. lividans/ps VB3310 tylosin-resistant colonies are isolated, cultured and identified according to known procedures.

Representative transfectants constructed in accordance with the foregoing teaching of Example 10 include, but are not limited to, the following transfectants listed in Table 3.

Table 3

Representative Transfectants

1. Streptomyces R/R[1] wherein R is ambofaciens, griseofuscus and lividans and wherein R[1] independently is a phage from the group consisting of phages pKC3310 and pKC3311.

We claim:

1. A method for selecting a recombinant DNA-containing Streptomyces host cell, said method comprising:

(a) transforming a tylosin-sensitive, restrictionless Streptomyces host cell with a recombinant DNA cloning vector capable of autonomous replication or integration in said Streptomyces host cell, said vector comprising a DNA sequence that confers resistance to tylosin, and (b) culturing said transformed cell under growth conditions suitable for selection for tylosin resistance, subject to the limitation that said host cell is susceptible to transformation, cell division and culture.

2. The method of claim 1 wherein the recombinant DNA cloning vector is a plasmid.

3. The method of claim 1 wherein the recombinant DNA cloning vector is a phage.

4. The method of claim 2 wherein the plasmid is selected from the group consisting of pSVB2, pSVB12, pSVB23, pSVB16, pSVB18, pSVB20 and pSVB22.

5. The method of claim 2 wherein the plasmid is pSVB2.

6. The method of claim 2 wherein the plasmid is pSVB12.

7. The method of claim 2 wherein the plasmid is pSVB23.

8. The method of claim 2 wherein the plasmid is pSVB16.

9. Themethod of claim 2 wherein the plasmid is pSVB18.

10. The method of claim 2 wherein the plasmid is pSVB20.

11. The method of claim 2 wherein the plasmid is pSVB22.

12. The method of claim 3 wherein the phage is selected from the group consisting of pSVB3310 and pSVB3311.

13. The method of claim 1 wherein the transformed Streptomyces host cell is selected from the group consisting of Streptomyces ambofaciens, Streptomyces aureofaciens, Streptomyces griseofuscus, Streptomyces lividans, Streptomyces cinnamonensis and Streptomyces [toyocaenisis] *toyocaensis.*

14. The method of claim 13 wherein the transformed host cell is Streptomyces griseofuscus/pSVB2.

15. The method of claim 13 wherein the transformed host cell is Streptomyces griseofuscus/pSVB12.

16. The method of claim 13 wherein the transformed host cell is Streptomyces griseofuscus/pSVB23.

17. The method of claim 13 wherein the transformed host cell is Streptomyces griseofuscus/pSVB16.

18. The method of claim 13 wherein the transformed host cell is Streptomyces griseofuscus/pSVB18.

19. The method of claim 13 wherein the transformed host cell is Streptomyces griseofuscus/pSVB20.

20. The method of claim 13 wherein the transformed host cell is Streptomyces griseofuscus/pSVB22.

21. The method of claim 13 wherein the transformed host cell is Streptomyces lividans/pSVB2.

22. The method of claim 13 wherein the transformed host cell is Streptomyces lividans/pSVB12.

23. The method of claim 13 wherein the transformed host cell is Streptomyces lividans/pSVB23.

24. The method of claim 13 wherein the transformed host cell is Streptomyces lividans/pSVB16.

25. The method of claim 13 wherein the transformed host cell is Streptomyces lividans/pSVB18.

26. The method of claim 13 wherein the transformed host cell is Streptomyces lividans/pSVB20.

27. The method of claim 13 wherein the transformed host cell is Streptomyces lividans/pSVB22.

28. A recombinant DNA cloning vector capable of autonomous replication or integration in a Streptomyces host cell, said vector comprising a DNA sequence that confers resistance to tylosin in a tylosin-sensitive Streptomyces host cell.

29. A vector *of* claim 28 which is selected from the group consisting of plasmids pSVB2, pSVB12, pSVB23, pSVB16, pSVB18, pSVB20 and pSVB22; and phages pSVB3310 and pSVB3311.

30. The vector of claim 29 that is plasmid pSVB2.

31. The vector of claim 29 that is plasmid pSVB12.

32. The vector of claim 29 that is plasmid pSVB23.

33. The vector of claim 29 that is plasmid pSVB16.

34. The vector of claim 29 that is plasmid pSVB18.

35. The vector of claim 29 that is plasmid pSVB20.

36. The vector of claim 29 that is plasmid pSVB22.

37. The vector of claim 29 that is plasmid pSVB3310.

38. A Streptomyces host cell transformed by a vector of claim 28, said Streptomyces host cell being tylosin-sensitive when not transformed with said vector.

39. The Streptomyces host cell of claim 38 transformed by a vector from the group consisting of plasmids pSVB2, [L pSVB12,] *pSVB12,* pSVB23, pSVB16, pSVB18, pSVB20 and pSVB22, and phage pSVB3310 and pSVB3311.

40. The transformed Streptomyces host cell of claim 39 that is Streptomyces ambofaciens.

41. The transformed Streptomyces host cell of claim 39 that is Streptomyces lividans.

42. The transformant of claim 40 that is Streptomyces ambofaciens/pSVB2.

43. The transformant of claim 41 that is Streptomyces lividans/pSVB3310.

44. A method for selecting a recombinant DNA-containing Nocardia host cell, said method comprising:

(a) transforming a tylosin-sensitive, restrictionless Nocardia host cell with a recombinant DNA cloning vector capable of autonomous replication or integration in said Noardia host cell, said vector comprising a DNA sequence that confers resistance to tylosin, and (b) culturing said transformed cell under growth conditions suitable for selection for tylosin resistance, subject to the limitation that said host cell is susceptible to transformation, cell division and culture.

45. The method of claim 44 wherein the recombinant DNA cloning vector is a plasmid.

46. A Nocardia host cell transformed by a recombinant DNA cloning vector capable of autonomous replication or integration in said Nocardia host cell, said vector comprising a DNA sequence that confers resistance to tylosin in a tylosin-sensitive Nocardia host cell, said Nocardia host cell being tylosin-sensitive when not transformed with said vector.

*47. A recombinant DNA comprising a DNA sequence capable of conferring tylosin resistance on a Streptomyces or Nocardia host cell.*

*48. The recombinant DNA of claim 47 wherein said DNA sequence is isolated from Streptomyces fradiae.*

*49. A recombinant DNA cloning vector comprising the DNA fragment of claim 48.*

*50. A Streptomyces host cell transformed by a vector of claim 49.*

*51. A DNA fragment of claim 48 which is a tylosin resistance-conferring restriction fragment of plasmid pSVB2.*

*52. A recombinant DNA cloning vector comprising the DNA fragment of claim 51.*

*53. A Streptomyces host cell transformed by a vector of claim 52.*

*54. The DNA fragment of claim 51 which is the ~2.6 kb KpnI restriction fragment of plasmid pSVB2.*

*55. A recombinant DNA cloning vector comprising the DNA fragment of claim 54.*

*56. A Streptomyces host cell transformed by a vector of claim 55.*

* * * * *